US006576665B2

United States Patent
Dennett, Jr. et al.

(10) Patent No.: US 6,576,665 B2
(45) Date of Patent: Jun. 10, 2003

(54) ENCAPSULATED CALCIUM ACETATE CAPLET AND A METHOD FOR INHIBITING GASTROINTESTINAL PHOSPHOROUS ABSORPTION

(75) Inventors: Edmund V. Dennett, Jr., Milton, MA (US); Robert M. Raleigh, Jr., Pembroke, MA (US); Bruce H. Aronson, Sharon, MA (US)

(73) Assignee: Braintree Laboratories, Inc., Braintree, MA (US)

( * ) Notice: Subject to any disclaimer, the term of this patent is extended or adjusted under 35 U.S.C. 154(b) by 118 days.

(21) Appl. No.: 09/824,949

(22) Filed: Apr. 3, 2001

(65) Prior Publication Data

US 2002/0173544 A1 Nov. 21, 2002

(51) Int. Cl.$^7$ .................. A01N 37/00; A61K 31/19
(52) U.S. Cl. ............................ 514/557; 429/602
(58) Field of Search .................. 514/557; 424/602

(56) References Cited

U.S. PATENT DOCUMENTS

| | | |
|---|---|---|
| 4,017,424 A | 4/1977 | Johnson et al. |
| 4,071,331 A | 1/1978 | Johnson et al. |
| 4,140,493 A | 2/1979 | Johnson et al. |
| 4,508,893 A | 4/1985 | Koyama et al. |
| 4,870,105 A * | 9/1989 | Fordtran ............... 514/557 |
| 5,347,046 A | 9/1994 | White et al. |
| 5,603,971 A | 2/1997 | Porzio et al. |
| 5,767,107 A | 6/1998 | Chaundy et al. |
| 5,897,897 A | 4/1999 | Porzio et al. |
| 6,187,351 B1 | 2/2001 | Porzio et al. |
| 6,201,053 B1 | 3/2001 | Dieckmann et al. |

OTHER PUBLICATIONS

United States Pharmacoepia 25 "Bulk Density" pp. 1981–1982.*

* cited by examiner

*Primary Examiner*—Michael G. Hartley
*Assistant Examiner*—Robert M DeWitty
(74) *Attorney, Agent, or Firm*—Cesari and McKenna, LLP

(57) ABSTRACT

A composition for inhibiting gastrointestinal absorption of phosphorous in an individual. The composition includes a quantity of calcium acetate sufficient to bind the phosphorous in the gastrointestinal tract of the individual. The calcium acetate has a bulk density of between 0.50 kg/L and 0.80 kg/L and is dimensioned to form a caplet for fitting within a capsule in a manner that optimizes the volume of the capsule. Also provided is a method for administering the calcium acetate composition of the present invention to an individual to reduce phosphorous absorption by binding with the phosphorous in their gastrointestinal tract.

15 Claims, No Drawings

ENCAPSULATED CALCIUM ACETATE CAPLET AND A METHOD FOR INHIBITING GASTROINTESTINAL PHOSPHOROUS ABSORPTION

BACKGROUND OF THE INVENTION

1. Field of the Invention

The present invention relates to the field of oral pharmaceutical compositions. More particularly, the present invention relates to an encapsulated calcium acetate caplet, and to a method for binding and inhibiting gastrointestinal absorption of phosphorous using an encapsulated calcium acetate caplet.

2. Background Information

A major focus of research and development efforts in the pharmaceutical industry is on the formulation of acceptable oral pharmaceutical compositions. More particularly, these efforts are concentrated on making oral pharmaceuticals that are palatable to the consumer. Chief among the concerns of pharmaceutical manufacturers in this area is the development of drugs that are as palatable as they are efficacious. The importance of these research efforts is greatest where the pharmaceuticals at issue are intended to ameliorate a patient's medical condition or alleviate their symptoms in cases of terminal illness. Chronic renal failure is one example of such an illness.

In cases of chronic renal failure, hyperphosphatemia, or excess phosphorus retention, plays a major role in the development of secondary hyperparathyroidism and osteodystrophy. Antacids or prescription medications are commonly used to manage or prevent hyperphosphatemia by binding dietary phosphorus and, thus, preventing its absorption into the gastrointestinal tract.

Phosphorous binders bind phosphorus in the form of a phosphorous ion within the stomach and intestines. This process is thought to result from a chemical reaction between dietary phosphorus and the cation present in the binder compound. The reaction causes the formation of insoluble and hence unabsorbable phosphate compounds. The cation in some phosphorous binders is aluminum or calcium. Despite their capacity for binding phosphorous, large quantities of antacids must be ingested over a long period of time for them to be effective. Therefore, dosage size and palatability are particularly important for patients with chronic renal disease.

Prescription medications typically effective in managing or preventing hyperphosphatemia include calcium acetate. Calcium acetate treatment is one of the most effective methods for management of chronic renal disease. When administered orally, calcium acetate is more effective than any other calcium-containing binder in binding phosphorus. Used alone or in combination with other materials, calcium acetate binds phosphorus in the gastrointestinal tract and reduces the percentage of consumed phosphorus (i.e., of a given "dose" of phosphorus) which is absorbed into the bloodstream. This compound is most effective in reducing phosphorous absorption when it is administered close in time to food consumption. Despite these benefits, calcium acetate treatments heretofore known in the art have not been without their drawbacks.

Calcium acetate is a naturally occurring solid. Like most solids found in nature, the bulk density of calcium acetate varies according to its source. Bulk density is the density, typically of a solid, as poured or passively filled into a measurement device. Bulk density can be determined by measuring the volume of a known mass (i.e., 125 g) of powder that has been passed into a graduated cylinder, followed by five "tamps" of the cylinder from a height of one (1) inch. Alternatively, it may be determined by measuring that volume of the known mass that has been passed through a volume measuring apparatus into a cup. While densities are normally expressed in grams per $cm^3$, where measured in graduated cylinders, the bulk density of powder volumes are expressed in grams per mL, where $cm^3$ and mL are equivalent volume units.

United States Pharmacopoeia (USP) is a widely recognized organization that sets some of the standards that pharmaceutical manufacturers must meet to sell their drugs and drug compounds in the United States. USP standards include procedures for the physical tests that must be performed on drugs and drug compounds to ensure compliance with the specific requirements set forth within these standards. USP #24 defines some of these standards for calcium acetate tablets. For example, physical test #711 on page 1941 of USP #24 sets forth the test to determine compliance with the dissolution standard set forth for calcium acetate tablets. USP #24 and #711 are incorporated herein by reference.

Pharmaceutical manufacturers in the art have heretofore used calcium acetate raw materials to form calcium acetate medications without regard to the density of the raw material fractions used. The result of this practice is that the manufacturers have been unable to produce a calcium acetate capsule or tablet of the usual dosage amount that is less than #00 in size, while passing test #711. An unfortunate consequence of the intrinsic characteristics of calcium acetate, and the practice of the pharmaceutical industry, is that patients needing this medication, such as end stage renal disease patients have heretofore found such medications due to their bulk size difficult to swallow. A second, equally undesirable characteristic of calcium acetate is that it has a chalky taste that is very unpleasant to the palate and is difficult to mask. Consequently, despite the obvious benefits of calcium acetate-based treatments, patients would typically fail to take the proper doses of their medicine, or turn to antacids as an alternative to these difficult-to-swallow unpalatable medications.

Calcium acetate compositions were heretofore no more desirable due to the dosing sizes, dosing requirements and the unpleasant taste associated with consumption of these medications. Accordingly, an encapsulated caplet that provides an effective dosage of medication for the treatment and management of terminal illnesses, without the risk of dosage side effects, is desired. An encapsulated caplet that also seals the taste of the medication and compresses the medication to ease or reduce the dosage volume necessary for effective illness treatment or management is desired, as well.

SUMMARY OF THE INVENTION

The present invention relates to a composition for binding phosphorous within the gastrointestinal tract of an individual and, thus, reducing phosphorus absorption in an individual's intestine. The present invention also relates to a method for binding phosphorous in the gastrointestinal tract of an individual to reduce phosphorous absorption therefrom. Moreover, the present invention relates to a method for reducing serum phosphate levels, since phosphorous is bound in the gastrointestinal tract and phosphorous absorption is lower than would otherwise occur. The composition and method of the present invention are particularly useful in the treatment and prevention of hyperphosphatemia in individuals with end stage renal disease. The composition and method of the present invention are also useful in the treatment and prevention of any other disease in which the ability to excrete phosphorus from the body (e.g., in the urine) is impaired.

The composition of the present invention includes a quantity of calcium acetate, having a specific bulk density range, that is sufficient to bind the phosphorous in the gastrointestinal tract of an individual. The calcium acetate composition is dimensioned to form a caplet for fitting within a capsule in a manner that optimizes the volume of the capsule, i.e., fills the internal volume of the capsule substantially completely. Insertion of the calcium acetate composition within the capsule masks the unpleasant and unpalatable taste of the enclosed caplet.

The method of the present invention comprises administering the calcium acetate composition, in the caplet-within-capsule form, to an individual to bind with the phosphorous in their gastrointestinal tract. Administration of the calcium acetate composition of the present invention according to the method described herein is associated with enhanced patient compliance and fewer side effects than is evident in administering presently available calcium acetate medications and phosphorus binders. This improved patient compliance with phosphate-binding ingestion will improve management of the disease process.

DETAILED DESCRIPTION OF AN ILLUSTRATIVE EMBODIMENT

The present invention takes advantage of the surprising discovery that, by selecting calcium acetate raw materials within a particular range of bulk densities, it is possible to compress and dimension the raw material to form a calcium acetate caplet, capsule or tablet that is smaller than heretofore formed and is more easily ingested. More particularly, the selection of a particular density range of calcium acetate permits the compression and dimensioning of the raw material to form a caplet that optimally fits within and substantially completely fills a capsule.

The present invention relates to an orally administrable calcium acetate composition that is useful in reducing phosphorus absorption in the gastrointestinal tract. More particularly, the composition consists of a quantity of calcium acetate having a bulk density of between 0.50 kg/L and 0.80 kg/L that dissolves by at least 85% in less than 15 minutes as specified in USP #24 at 50 to 100 RPM, apparatus 1 or 2, using purified water as diluent. As set forth in Table 1, a calcium acetate composition having a bulk density of between 0.55 kg/L and 0.75 kg/L is desirable as it has optimal pharmaceutical properties, including compliance with USP #24. More preferably, the bulk density of the calcium acetate used in the composition of the present invention is between 0.60 kg/L and 0.70 kg/L, and the dosage amount is equivalent to approximately 667 mg, or approximately 333.3 mg, as desired, in a size #0 or size #2 capsule, respectively.

Table 1

| Bulk Density (kg/L) | Meets Caplet Target Weight | Displays Tablet Capping | Displays Tablet Picking | Passes Dissolution |
|---|---|---|---|---|
| <0.55 | No | No | Yes | No |
| 0.55 to 0.75 | Yes | No | No | Yes |
| >0.75 | Yes | Yes | No | No |

As illustrated in this table, column 2 indicates whether a calcium acetate caplet of a given bulk density can be compressed to meet the target weight of 667 mg and fit into a #0 or a target weight of 333.5 mg in a #2 size capsule. Column 3 indicates whether the calcium acetate caplet of the noted bulk density can be compressed to meet a target weight of 667 mg and fit into a #0 capsule, or a target weight of 333.5 mg in fit into a #2 size capsule, without an unacceptable incidence of "capping" (i.e., splitting along a plane parallel to the long axis of the capsule). Column 4 indicates whether the calcium acetate caplet of the given bulk density can be compressed to meet a target weight of 667 mg and fit into a #0 capsule, or a target weight of 333.5 mg in fit into a #2 size capsule, without an unacceptable incidence of "picking" (i.e., loss of small punctuate flecks of material from its surface). Column 5 indicates whether the calcium acetate caplet of the given bulk density will pass the dissolution specifications for calcium acetate upon being compressed to a size to fit 667 mg into a #0 or 333.5 mg into a #2 size capsule. Throughout this discussion, 667 mg and 333.5 mg refer to calcium acetate, anhydrous basis. An equivalent amount of calcium acetate monohydrate basis weighs 708 mg or 354 mg, respectively.

The calcium acetate composition of the present invention is optionally dimensioned to form a delivery vehicle comprising a tablet, a capsule or a caplet. Of these delivery vehicles, capsules are preferred as they completely coat and envelop the caplet until the capsule reaches the gastrointestinal tract, or stomach. Once within the stomach, the capsule shell is dissolved and the medication is released and binds the phosphorous in the intestine.

The capsule is formed from any material which, when wetted by the individual's saliva or by accompanying water or other flushing fluid, facilitates the ingestion of the caplet. More preferably, the capsule shell consists of a gelatin material as a gelatin capsule better masks the bitter taste of the calcium acetate medication. The gelatin capsule is also preferred as it provides a more palatable surface to the medication that makes it easier to swallow and pass into the digestive system.

In one embodiment, the calcium acetate is dimensioned to form a caplet for fitting within a volume defined by a #0 size capsule in a manner that optimizes the volume of the capsule, i.e., fills the internal volume of the capsule substantially completely. In another embodiment, the calcium acetate is dimensioned to form a caplet for fitting within and substantially completely filling a volume defined by a #2 size capsule.

The composition of the present invention preferably consists of approximately 667 mg of calcium acetate dimensioned to form a caplet for fitting within a volume defined by #0 size capsule in a manner that optimizes the volume of the capsule. In another embodiment, the composition preferably consists of approximately 333.5 mg of calcium acetate dimensioned to form a caplet for fitting within and substantially completely filling a volume defined by #2 size capsule.

The present invention also relates to a method of inhibiting gastrointestinal phosphorus absorption. More particularly, the method of the present invention facilitates the oral administration of calcium acetate to effectively bind with phosphorus in an individual's gastrointestinal tract, and reduce the serum absorption of phosphorous. Additionally, the method of the present invention facilitates the reduction in phosphorous absorption that is noted when the composition is consumed at or near mealtime, the time at which foods and beverages are ingested.

Administering the calcium acetate composition of the present invention will also reduce the absorption of dietary phosphorus, thereby reducing the risks of adverse effects (e.g., bone disease and secondary hyperparathyroidism) observed in individuals (e.g., chronic renal patients) in whom the ability to excrete phosphorus in the urine is impaired.

According to the method of the present invention, a quantity of calcium acetate having a bulk density of between 0.50 kg/L and 0.80 kg/L is administered in sufficient quantities to reduce phosphorus absorption in the gastrointestinal tract. The calcium acetate is administered orally, and is preferably dimensioned to form a caplet for fitting within a capsule in a manner that optimizes the volume of the capsule. The caplet dissolves in less than 15 minutes at 50 to 100 RPM, apparatus 1 or 2, in purified water (USP #24).

The foregoing description has been directed to specific embodiments of this invention. It will be apparent, however, that other variations and modifications may be made to the described embodiments with the attainment of some or all of their advantages. Accordingly, this description should be taken only by way of example and not by way of limitation. It is the object of the appended claims to cover all such variations and modifications as come within the true spirit and scope of the invention.

Additional excipients, fillers, dispersants, lubricants and the like may be added to the composition of the present invention to improve its manufacture, and such modifications will be recognized as being within thew spirit and the scope of the present invention.

What is claimed is:

1. A composition for binding phosphorous within the gastrointestinal tract of an individual, the composition comprising:
    a quantity of calcium acetate sufficient to bind the phosphorous in the gastrointestinal tract of the individual, the calcium acetate having a bulk density of between about 0.55 kg/L and about 0.75 kg/L, and where the quantity of calcium acetate is compressed to form a caplet for fitting within a capsule in a manner which optimizes the volume of the capsule, and where at least about 85% of said compressed calcium acetate dissolves in not more than 15 minutes when tested according to USP standard #24, test #711 at 50 to 100 RPM, apparatus 1 or 2.

2. The composition of claim 1, wherein the quantity of calcium acetate is a dosage amount equivalent to approximately 667 mg of calcium acetate, anhydrous basis.

3. The composition of claim 1, wherein the calcium acetate has a bulk density of between 0.60 kg/L and 0.70 kg/L.

4. The composition of claim 1, wherein the calcium acetate is dimensioned to form a caplet for fitting within a volume defined by #0 size capsule in a manner that optimizes the volume of the capsule.

5. The composition of claim 4, wherein 667 mg of anhydrous calcium acetate are dimensioned to form the caplet for fitting within the volume defined by #0 size capsule.

6. The composition of claim 4, wherein 708 mg of monohydrous calcium acetate are dimensioned to form the caplet for fitting within the volume defined by #0 size capsule.

7. The composition of claim 1, wherein the calcium acetate is dimensioned to form a caplet for fitting within a volume defined by #2 size capsule in a manner that optimizes the volume of the capsule.

8. The composition of claim 7, wherein 333.3 mg of anhydrous calcium acetate are dimensioned to form the caplet for fitting within the volume defined by #2 size capsule.

9. The composition of claim 4, wherein 354 mg of monohydrous calcium acetate are dimensioned to form the caplet for fitting within the volume defined by #2 size capsule.

10. A composition for absorbing phosphorous within the gastrointestinal tract of an individual, the composition comprising:
    approximately 667 mg calcium acetate, anhydrous basis, having a bulk density of between about 0.55 kg/L and about 0.75 kg/L, and where the calcium acetate is compressed to form a caplet for fitting within the volume of a #0 capsule, and where at least about 85% of said compressed calcium acetate dissolves in not more than 15 minutes when tested according to USP standard #24, test #711 at 50 to 100 RPM, apparatus 1 or 2.

11. A composition for absorbing phosphorous within the gastrointestinal tract of an individual, the composition comprising:
    approximately 333.5 mg of calcium acetate, anhydrous basis, having a bulk density of between about 0.55 kg/L and about 0.75 kg/L, said calcium acetate being compressed to form a caplet for fitting within a volume of a #2 size capsule, and where at least about 85% of said calcium acetate in said capsule dissolves in not more than 15 minutes when tested according to USP #24, test #711 at 50 to 100 RPM, apparatus 1 or 2.

12. A method for binding phosphorous in the gastrointestinal tract of an individual, the method comprising at least the step of:
    administering a composition for binding phosphorous, the composition comprising a quantity of calcium acetate sufficient to bind with the phosphorous in the gastrointestinal tract of the individual,
    the calcium acetate having a hulk density of between about 0.55 kg/L and about 0.75 kg/L, and being compressed to form a caplet for fitting within a capsule in a manner which optimizes the volume of the capsule, and where at least about 85% of said calcium acetate in said capsule dissolves in not more than 15 minutes when tested according to USP #24, test #711 at 50 to 100 RPM, apparatus 1 or 2.

13. The method for binding phosphorous in the gastrointestinal tract of an individual according to claim 12, wherein about 667 mg of calcium acetate, anhydrous basics, having a bilk density of between about 0.55 kg/L and about 0.75 kg/L, is compressed to form a caplet for fitting within a volume defined by #0 size capsule.

14. The method of claim 12, wherein the calcium acetate has a bulk density of between 0.60 kg/L and 0.70 kg/L.

15. The method for binding phosphorous in the gastrointestinal tract of an individual according to claim 12, wherein 335.5 mg of calcium acetate, anhydrous basis, having a bulk density of between about 0.55 kg/L and about 0.75 kg/L, is compressed to form a caplet for fitting within a volume defined by #2 size capsule.

* * * * *

UNITED STATES PATENT AND TRADEMARK OFFICE
CERTIFICATE OF CORRECTION

PATENT NO. : 6,576,665 B2 Page 1 of 1
DATED : June 10, 2003
INVENTOR(S) : Edmund V. Dennett, Jr. et al.

It is certified that error appears in the above-identified patent and that said Letters Patent is hereby corrected as shown below:

Column 6,
Line 52, replace "bilk" with -- bulk --.

Signed and Sealed this

Twenty-second Day of July, 2003

JAMES E. ROGAN
*Director of the United States Patent and Trademark Office*